United States Patent [19]
Hempowitz et al.

[11] 3,940,623
[45] Feb. 24, 1976

[54] APPARATUS FOR MEASURING THE PROPORTION OR QUANTITY OF A COMPONENT IN A RADIATION-TRANSPARENT MIXTURE

[75] Inventors: Günter Hempowitz; Jochen Pokar, both of Julich, Germany

[73] Assignee: Uranit, Uran-Isotopentrennungs-Gesellschaft m.b.H., Julich, Germany

[22] Filed: Oct. 7, 1974

[21] Appl. No.: 512,866

[30] Foreign Application Priority Data
Oct. 5, 1973 Germany............................ 2350004

[52] U.S. Cl................................. 250/343; 356/184
[51] Int. Cl.²........................................ G01M 21/26
[58] Field of Search .......... 250/343, 344, 345, 346, 250/373; 356/184

[56] References Cited
UNITED STATES PATENTS
3,435,209 3/1969 Keahl................................. 250/343
3,740,144 6/1973 Walker ................................ 356/97

FOREIGN PATENTS OR APPLICATIONS
896,736 5/1962 United Kingdom................ 356/184

*Primary Examiner*—Craig E. Church
*Attorney, Agent, or Firm*—Spencer & Kaye

[57] ABSTRACT

For measuring the proportion or quantity of a component in a radiation-transparent mixture, a beam is passed through the mixture and subsequently split by a beam splitter into a measuring beam and a reference beam. The measuring beam is passed through a narrow-band interference filter which has a transmitting wavelength that corresponds to a discrete absorption wavelength of the component. This filter is oscillated in a range of oscillation which traverses the absorption maximum. The reference beam is passed through a narrow-band interference filter which has a transmitting wavelength that differs from the absorption wavelength of the component. Subsequently, the radiation intensities of the measuring beam and the reference beam are separately detected and their difference is formed. This difference is a function of the proportion or quantity of the component.

2 Claims, 4 Drawing Figures

APPARATUS FOR MEASURING THE PROPORTION OR QUANTITY OF A COMPONENT IN A RADIATION-TRANSPARENT MIXTURE

BACKGROUND OF THE INVENTION

This invention relates to an apparatus for measuring the proportion or quantity of a component in a radiation-transparent mixture by means of discrete radiation absorption. The beam passing through the mixture is split into a measuring beam and a reference beam. The measuring beam is passed through a narrow-band interference filter, the transmitting wavelength of which corresponds to a discrete absorption wavelength of the component to be tested. The reference beam is passed through a narrow-band interference filter, the transmitting wavelength of which is different from the absorption wavelength of the component to be tested. The difference between the radiation intensities of measuring beam and reference beam is utilized as the measure for the proportion or quantity, as the case may be, of the component to be tested.

A measuring method which is based on infra-red absorption and which relates to the determination of individual components of a liquid or gaseous mixture, is described in J. J. Howarth et al., *An Infra-red Process Analyser Based on Interference Filters*, JOURNAL OF SCIENTIFIC INSTRUMENTS, Volume 42, 1965, pages 526–528. According to the method described in this article, two branch beams are passed through a measuring filter and a reference filter and subsequently they are directed by means of appropriate deflecting systems to a common detector. Between the detector and the filters there is arranged a chopper which alternately transmits the measuring beam and the reference beam. As set forth in the first paragraph in the right-hand column on page 528 of the above-identified article, by virtue of an appropriate filter combination an indicating sensitivity to hydrogen fluoride down to 50 parts per million was obtained. In the same paragraph of the article it is indicated that the interference bands and the absorption bands have to match exactly.

Particularly in the use of narrow-band interference filters it has been found to be difficult to adjust the sensitivity maximum in a permanent manner by an appropriate setting of the filters. Because of the steep flanks of the absorption lines of the material and the transmission lines of the filters, slight external influences, such as small mechanical vibrations and the like, suffice to lower the sensitivity and thus the accuracy of value indication.

SUMMARY OF THE INVENTION

It is an object of the invention to provide an improved apparatus of the above-outlined type for maintaining the maximum sensitivity over relatively long periods of time.

This object and others to become apparent as the specification progresses, are accomplished by the invention, according to which, briefly stated, the filter for the measuring beam is moved periodically back and forth in a path that traverses the absorption maximum. The range of oscillation is expediently selected to be of such a magnitude that at both ends of the range a minimum is indicated. The alternating swinging motion may have a relatively low frequency of for example 0.1 Hz, while the chopper frequency is maintained at about 780 Hz. For an electronic signal processing, this latter frequency should not be a multiple of the line frequency (for example, 60 Hz). During the course of each swinging motion, the filter momentarily assumes a certain angle with respect to the beam in which the absorption line and the transmitting line coincide. The wavelength of the transmitting line has its maximum at an angle of approximately 90° between the beam and the filter surface; in case of a deviation from this perpendicular penetration of radiation, the transmitting line shifts towards lower wavelengths. Thus, according to the invention, it is proposed to use a measuring filter, the transmitting wavelength of which, in case of a perpendicular penetration of radiation, is slightly above the absorption wavelength of the component to be tested so that it is ensured that during each swing of the filter the absorption maximum is scanned.

For the reference beam, on the other hand, a filter should be selected, whose transmitting wavelength is below the utilized absorption line of the component to be tested and, in particular, is below the band range.

BRIEF DESCRIPTION OF THE DRAWINGS

FIG. 1a is a schematic fragmentary illustration of a component of the FIG. 1 structure, as viewed in a direction parallel to the beam axes.

DESCRIPTION OF THE PREFERRED EMBODIMENT

Figure 1:
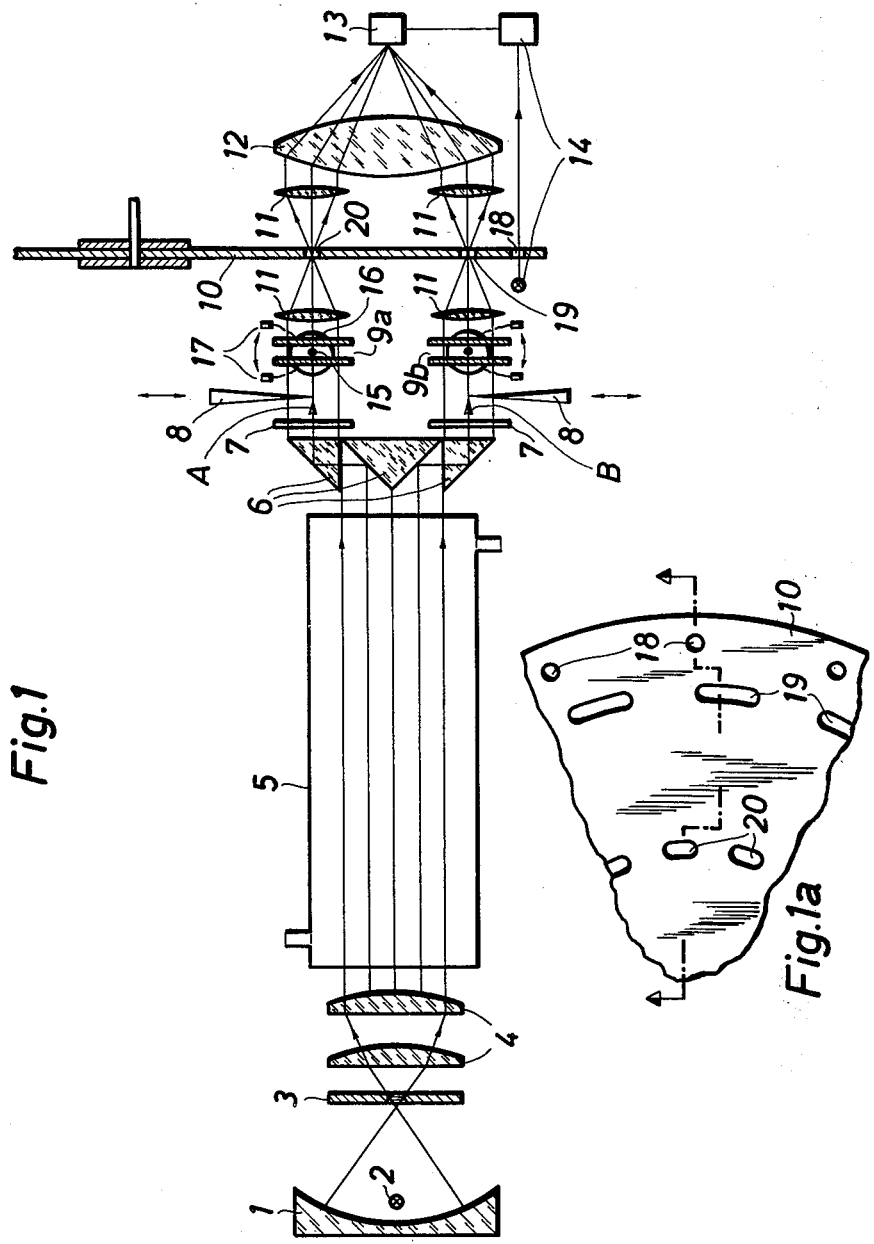
FIG. 1 is a schematic illustration of the optical arrangement of a preferred embodiment of a measuring apparatus, as viewed in a direction perpendicular to the beam axes, adapted to perform the method according to the invention.

Turning now to FIG. 1, the apparatus schematically illustrated therein includes a concave reflector mirror 1 associated with a light source 2, such as a halogen lamp, a slit screen 3, two plane-convex lenses 4, a test tube 5 containing the material mixture through which the beam is passed, a beam splitting prism system 6, two slit screens 7 in the path of the one and the other split beam, and two split beam compensators 8. The apparatus further comprises measuring beam and reference beam filters 9a and 9b, respectively, each comprising two serially arranged individual elements. There are further provided a beam chopper disc 10, two bi-convex lenses 11 for each split beam, arranged in front of and behind the chopper disc 10, a collector lens 12, a detector 13 with an after-connected signal processing and evaluating system as well as a device 14 for receiving, processing and feeding the chopper reference signal. The measuring filter 9a is provided with a rotary shaft 15 oriented perpendicularly to the beam axis. The shaft 15 is connected to a drive motor 16 for imparting to the shaft 15 an oscillating motion of a frequency of about 0.1 Hz. For limiting the amplitude (range) of oscillation and to reverse the direction of motor rotation to obtain an oscillating motion, there are provided limit switches 17 for controlling the motor 16. These limit switches may be arranged at the opposite ends of the range of oscillation and thus are actuated by the oscillating filter each time the latter assumes an extreme position at the ends of its travelling path.

It is expedient to oscillate the reference beam filter 9b inphase with the motion of the measuring beam filter 9a in order to compensate for intensity fluctuations that may occur due to the swinging motions of the filter 9a. For oscillating the reference beam filter 9b, the same type of mechanism may be used as described in connection with the oscillation of the measuring filter 9a.

Also referring now to FIG. 1a, the chopper disc 10 which is driven with a frequency of, for example, 780 Hz, is provided in the vicinity of its outer edge, along an outer circle, with several uniformly spaced openings 18 for allowing passage of a reference signal generated by the device 14. Along a middle circle and an inner circle, respectively, there are arranged, in an out-of-phase relationship, the same number of apertures 19 and 20 for the passage of the reference beam (arrow B in FIG. 1) and for the measuring beam (arrow A in FIG. 1). In this manner the measuring beam and the reference beam impinge alternatingly on the detector 13. By means of an after-connected electronic equipment both signals are processed (including comparison) and applied to an indicating or recording apparatus in a manner known by itself.

Figure 2:
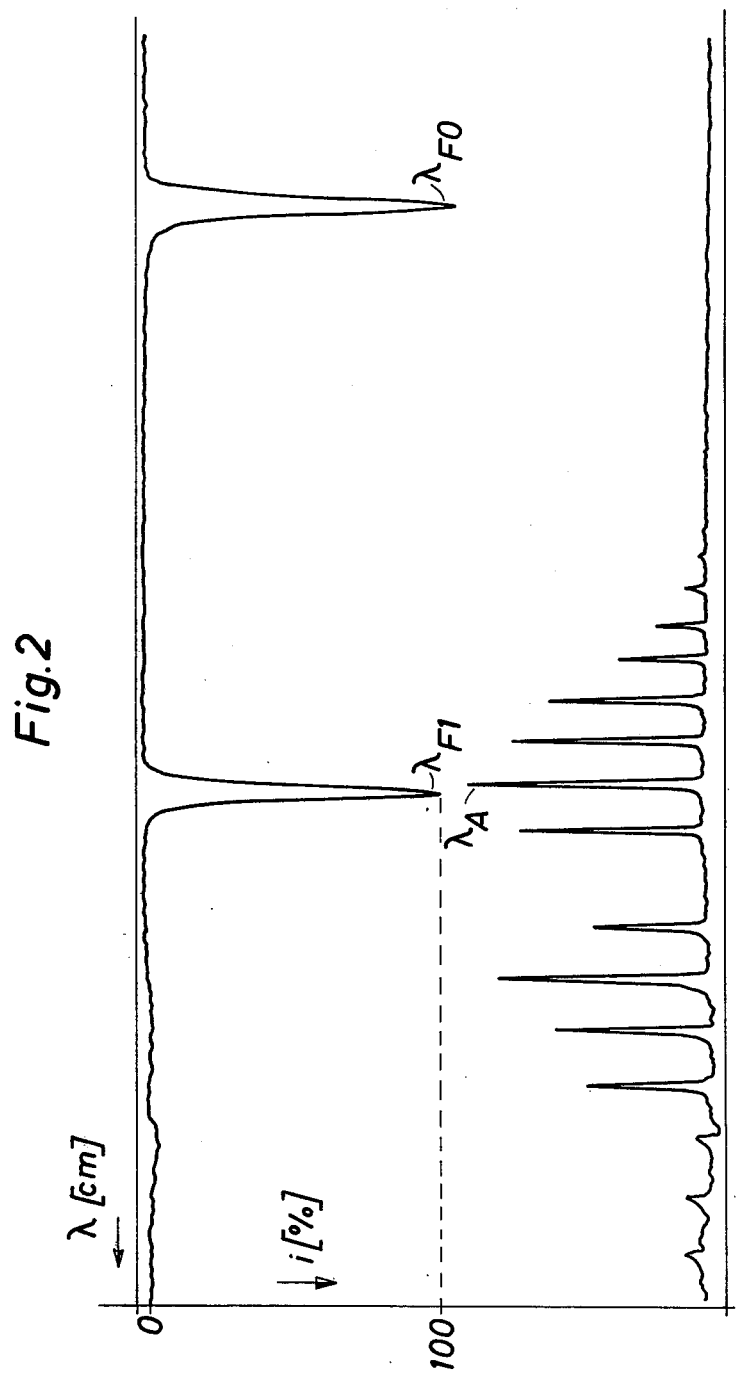
FIG. 2 is a diagram in which the hydrogen fluoride (HF) absorption bands containing the characteristic absorption lines and the transmission lines of the measuring filter and of the reference filter are plotted as a function of the wavelength.

As it may be observed in FIG. 2, the HF spectrum shows several absorption lines in a certain wavelength range. To one of these absorption lines there is assigned the measuring filter whose maximum transmitting wavelength $\lambda_{F1}$ lies somewhat above the absorption maximum $\lambda_A$. The reference filter has the same characteristics as the measuring filter; its transmitting wavelength $\lambda_{F0}$ lies, however, below the HF absorption spectrum (of the HF rotary swinging band). By virtue of the oscillation of the measuring filter, $\lambda_{F1}$ shifts towards lower wavelengths.

Figure 3:
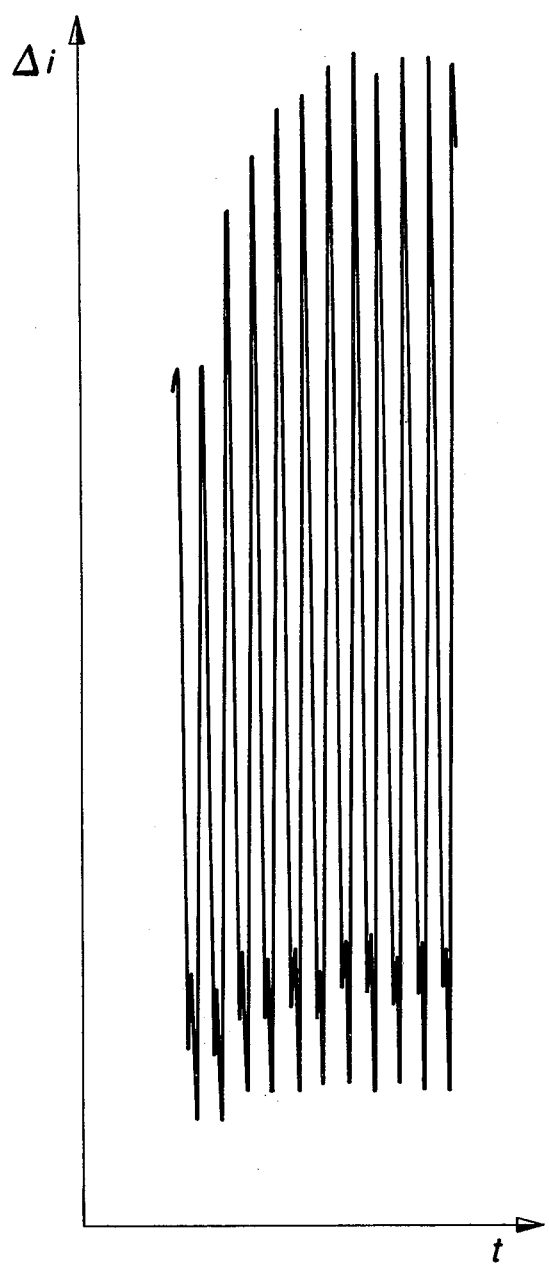
FIG. 3 illustrates a diagram in which the difference of the measuring signals is plotted as a function of time.

As $\lambda_{F1}$ approaches $\lambda_A$, the intensity $i$ of the measuring beam impinging on the detector 13 decreases. This phenomenon may be observed in FIG. 3. In this diagram the difference of the intensities $\Delta i$ between the measuring and reference beams is shown as a function of the time $t$. The sequence of the intensity peaks corresponds to the frequency of the filter-oscillating mechanism while the amplitudes of these peaks correspond to an HF-pressure alteration in the test tube. In the case illustrated, the maximum amplitude corresponds to an HF content of 1 mol percent HF in an HF/N$_2$ mixture.

It will be understood that the above description of the present invention is susceptible to various modifications, changes and adaptations, and the same are intended to be comprehended within the meaning and range of equivalents of the appended claims.

We claim:

1. In an apparatus for measuring the proportion or quantity of a component of a radiation transparent mixture by discrete radiation absorption, including means for passing a beam through the mixture; beam splitting means disposed downstream of the mixture with respect to the travelling direction of the beam for splitting the beam into a measuring beam and a reference beam; a first narrow-band interference filter arranged in the path of the measuring beam; a second narrow-band interference filter arranged in the path of the reference beam; means disposed downstream of the filters for separately detecting the radiation intensities of the measuring beam and the reference beam; and means for forming the difference between the two radiation intensities, the difference between the two radiation intensities being a function of the proportion and quantity of the component; the improvement wherein said first filter has a transmitting wavelength slightly above the discrete absorption wavelength of the component for a perpendicular penetration of radiation and said second filter has a transmitting wavelength outside the absorption spectrum of the component; further comprising means for oscillating said filters in phase in a range of oscillation in which said first filter traverses the absorption maximum.

2. An apparatus as defined in claim 1, wherein said first filter has two extreme positions which it assumes at opposite ends of its travelling path, said means for oscillating said first filter includes a drive shaft affixed to said filter and extending normal to the measuring beam impinging upon said first filter; a drive motor connected to said drive shaft for rotating the latter; and limit switches connected to said drive motor, said limit switches being arranged at the opposite ends of the oscillating path of said first filter for reversing said drive motor upon said first filter reaching either of its extreme positions.

* * * * *